(12) United States Patent
Zhang

(10) Patent No.: US 8,886,522 B2
(45) Date of Patent: *Nov. 11, 2014

(54) AUTOMATED EXTRACTION OF BIO-ENTITY RELATIONSHIPS FROM LITERATURE

(71) Applicant: The Florida State University Research Foundation, Inc., Tallahassee, FL (US)

(72) Inventor: Jinfeng Zhang, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 89 days.

This patent is subject to a terminal disclaimer.

(21) Appl. No.: 13/971,145

(22) Filed: Aug. 20, 2013

(65) Prior Publication Data

US 2013/0339005 A1 Dec. 19, 2013

Related U.S. Application Data

(63) Continuation-in-part of application No. 13/854,546, filed on Apr. 1, 2013.

(60) Provisional application No. 61/618,217, filed on Mar. 30, 2012.

(51) Int. Cl.
*G06F 19/24* (2011.01)
*G06F 17/27* (2006.01)

(52) U.S. Cl.
CPC ............. *G06F 19/24* (2013.01); *G06F 17/278* (2013.01)
USPC .......................................................... 704/9

(58) Field of Classification Search
USPC .......................................................... 704/9
See application file for complete search history.

(56) References Cited

U.S. PATENT DOCUMENTS

| 7,299,407 | B2 * | 11/2007 | Joshi et al. | 715/205 |
| 2005/0108001 | A1 * | 5/2005 | Aarskog | 704/10 |
| 2011/0213742 | A1 * | 9/2011 | Lemmond et al. | 706/13 |
| 2011/0270604 | A1 * | 11/2011 | Qi et al. | 704/9 |
| 2012/0143881 | A1 * | 6/2012 | Baker et al. | 707/750 |
| 2013/0262091 | A1 * | 10/2013 | Zhang | 704/9 |

OTHER PUBLICATIONS

Kann MG, Protein interactions and disease: computational approaches to uncover the etiology of diseases. Brief Bioinform. 2007. vol. 8 (No. 5):333-346.
Keshava Prasad et al., Human Protein Reference Database—2009 update. Nucleic Acids Res. 2009. vol. 37: D767-772.

(Continued)

*Primary Examiner* — Susan McFadden
(74) *Attorney, Agent, or Firm* — Nilay J. Choksi; Smith & Hopen, P.A.

(57) ABSTRACT

Automated, standardized and accurate extraction of relationships within text. Automatic extraction of such relationships/information allows the information to be stored in structured form so that it can be easily and accurately retrieved when needed. Such information can be used to build online search engines for highly specific and accurate information retrieval. The current invention discloses a novel approach to extract such information from raw text based on natural language processing (NLP) and graph theoretic algorithm. The novel method can be applied, for example, to extract protein-protein relationships in biomedical literature. The method can be easily extended to extract other biological relationships between biological terms such as proteins, genes, pathways, diseases and drugs. The method can also be applied to other information domains to extract other relationships.

20 Claims, 3 Drawing Sheets

(56) References Cited

OTHER PUBLICATIONS

Salwinski et al. The Database of Interacting Proteins: 2004 update. Nucleic Acids Res. 2004. vol. 32: D449-451.
Chatr-Aryamontri, et al. MINT: the Molecular INTeraction database. Nucleic Acids Res. 2007. vol. 35: D572-574.
Stark et al. BioGRID: a general repository for interaction datasets. Nucleic Acids Res. 2006. vol. 34: D535-539.
Mishra GR et al. Human protein reference database—2006 update. Nucleic Acids Res. 2006. vol. 34: D411-414.
Pagel P et al. The MIPS mammalian protein-protein interaction database. Bioinformatics. 2005. vol. 21 (No. 6): 832-834.
Beuming et al. PDZBase: a protein-protein interaction database for PDZ-domains. Bioinformatics. 2005. vol. 21 (No. 6): 827-828.
Alfarano et al. The Biomolecular Interaction Network Database and related tools 2005 update. Nucleic Acids Res. 2005. vol. 33: D418-424.
Mathivanan et al. An evaluation of human protein-protein interaction data in the public domain. BMC Bioinformatics. 2006. vol. 7 (Suppl 5): S19.
Aranda et al., The IntAct molecular interaction database in 2010. Nucleic Acids Res. 2010. vol. 38: D525-531.
Han et al, HPID: the Human Protein Interaction Database. Bioinformatics. 2004. vol. 20 (No. 15): 2466-2470.
Kuhn et al., Stitch: interaction networks of chemicals and proteins. Nucleic Acids Res. 2008. vol. 36: D684-688.
Griffith et al., ORegAnno: an open-access community-driven resource for regulatory annotation. Nucleic Acids Res. 2008. vol. 36: D107-113.
Gama-Castro et al., RegulonDB (version 6.0): gene regulation model of *Escherichia coli* K-12 beyond transcription, active (experimental) annotated promoters and Textpresso navigation. Nucleic Acids Res. 2008. vol. 36: D120-124.
Grote et al., Prodoric (release 2009): a database and tool platform for the analysis of gene regulation in prokaryotes. Nucleic Acids Res. 2009. vol. 37: D61-65.
Shahi et al., Argonaute—a database for gene regulation by mammalian microRNAs. Nucleic Acids Res. 2006. vol. 34: D115-118.
Sierro et al., DBTGR: a database of tunicate promoters and their regulatory elements. Nucleic Acids Res. 2006. vol. 34: D552-555.
Matys et al., Transfac: transcriptional regulation, from patterns to profiles. Nucleic Acids Res. 2003. vol. 31: 374-378.
Korbel et al., Systematic association of genes to phenotypes by genome and literature mining. PLoS Biol. 2005. vol. 3: e134.
Koike et al., Automatic extraction of gene/protein biological functions from biomedical text. Bioinformatics. 2005. vol. 21 (No. 7): 1227-1236.
Rzhetsky et al., Seeking a new biology through text mining. Cell. 2008. vol. 134: 9-13.
Jensen et al., Literature mining for the biologist: from information retrieval to biological discovery. Nat Rev Genet. 2006. vol. 7: 119-129.
Gonzalez et al., Mining gene-disease relationships from biomedical literature: weighting protein-protein interactions and connectivity measures. Pac Symp Biocomput. 2007. vol. 12:28-39.
Huang et al., Mining physical protein-protein interactions from the literature. Genome Biol. 2008. vol. 9 Suppl 2: S12.
Barrell et al., The GOA database in 2009—an integrated Gene Ontology Annotation resource. Nucleic Acids Res. 2008. vol. 37: D396-403.
Ceol et al., Linking entries in protein interaction database to structured text: the FEBS Letters experiment. FEBS Letters. 2008. vol. 582: 1171-1177.
Mottaz et al., Mapping proteins to disease terminologies: from UniProt to MeSH. BMC Bioinformatics. 2008. vol. 9 (Suppl 5): S3.
Wong et al., Protein Interactome Analysis for Countering Pathogen Drug Resistance. Journal of Computer Science and Technology. 2010. vol. 25: 124-130.
Tikk et al., A Comprehensive Benchmark of Kernel Methods to Extract Protein-Protein Interactions from Literature. PLoS Computational Biology. 2010. vol. 6 (Issue 7): e1000837.
Kano et al., Filling the gaps between tools and users: a tool comparator, using protein-protein interaction as an example. Pac Symp Biocomput. 2008. vol. 13: 616-627.
Bui et al., Extracting causal relations on HIV drug resistance from literature. BMC Bioinformatics. 2010. vol. 11: 101.
Bui et al., A hybrid approach to extract protein-protein interactions. Bioinformatics. 2011. vol. 27 (No. 2): 259-265.
Pyysalo et al. Comparative analysis of five protein-protein interaction corpora. BMC Bioinformatics. 2008. vol. 9 (Suppl 3): S6.
Krallinger et al., Assessment of the second BioCreative PPI task: automatic extraction of protein-protein interactions. Proceedings of the BioCreative Workshop. 2007: 41-54.
Krallinger et al., Overview of the protein-protein interaction annotation extraction task of BioCreative II. Genome Biol. 2008. vol. 9 (Suppl 2): S4.
Hu et al., Mining Hidden Connections among Biomedical Concepts from Disjoint Biomedical Literature Sets through Semantic-based Association Rule. International Journal of Intelligent System. 2010. vol. 25: 207-223.
Hu et al., Data Mining and Predictive Modeling of Biomolecular Network from Biomedical Literature Databases. IEEE/ACM Transactions on Computational Biology and Bioinformatics. 2007. vol. 4 (No. 2): 251-263.
Giles et al., Large-scale directional relationship extraction and resolution. BMC Bioinformatics. 2008. vol. 9 (Suppl 9): S11.
Skusa et al., Extraction of biological interaction networks from scientific literature. Brief Bioinform. 2005. vol. 6 (No. 3): 263-276.
C Blaschke et al., Automatic extraction of biological information from scientific text: protein-protein interactions. Proc Int Conf Intell Syst Mol Biol. 1999: 60-67.
NG et al., Toward Routine Automatic Pathway Discovery from On-line Scientific Text Abstracts. Genome Inform Ser Workshop Genome Inform. 1999. vol. 10: 104-112.
J Pustejovsky et al., Robust relational parsing over biomedical literature: extracting inhibit relations. Pac Symp Biocomput. 2002. pp. 362-373.
J M Temkin et al., Extraction of protein interaction information from unstructured text using a context-free grammar. Bioinformatics. 2003. vol. 19 (No. 16): 2046-2053.
J C Park et al., Bidirectional incremental parsing for automatic pathway identification with combinatory categorial grammar. Pac Symp Biocomput. 2001. vol. 6: 396-407.
J Thomas et al., Automatic extraction of protein interactions from scientific abstracts. Pac Symp Biocomput. 2000. vol. 5: 541-552.
Saric et al., Extraction of regulatory gene/protein networks from Medline. Bioinformatics. 2006. vol. 22 (No. 6): 645-650.
A Yakushiji et al., Event extraction from biomedical papers using a full parser. Pac Symp Biocomput. 2001. vol. 6: 408-419.
C Friedman et al., Genies: a natural-language processing system for the extraction of molecular pathways from journal articles. Bioinformatics. 2001. vol 17 (Suppl 1): S74-82.
G Leroy et al., Filling preposition-based templates to capture information from medical abstracts. Pac Symp Biocomput. 2002. vol. 7:350-361.
T Ono et al., Automated extraction of information on protein-protein interactions from the biological literature. Bioinformatics. 2001. vol. 17 (No. 2): 155-161.
Wong L, Pies, a protein interaction extraction system. Pac Symp Biocomput. 2001. vol. 6: 520-531.
Narayanaswamy et al., Beyond the clause: extraction of phosphorylation information from medline abstracts. Bioinformatics. 2005. vol. 21 (Suppl 1): i319-327.
M Huang et al., Discovering patterns to extract protein-protein interactions from full texts. Bioinformatics. 2004. vol. 20 (No. 18): 3604-3612.
Kim et al., Kernel approaches for genic interaction extraction. Bioinformatics. 2008. vol. 24 (No. 1): 118-126.
Malik et al., Combination of text-mining algorithms increases the performance. Bioinformatics. 2006. vol. 22 (No. 17): 2151-2157.

(56) References Cited

OTHER PUBLICATIONS

Jenssen et al., A literature network of human genes for high-throughput analysis of gene expression. Nat Genet. 2001. vol. 28: 21-28.

Stapley et al., Biobibliometrics: information retrieval and visualization from co-occurrences of gene names in Medline abstracts. Pac Symp Biocomput. 2000: 529-540.

Krallinger et al., Evaluation of text-mining systems for biology: overview of the Second BioCreative community challenge. Genome Biol. 2008. vol. 9 (Suppl 2): S1.

Hatzivassiloglou et al., Learning anchor verbs for biological interaction patterns from published text articles. Int J Med Inform. 2002. vol. 67: 19-32.

Kim et al., Pie: an online prediction system for protein-protein interactions from text. Nucleic Acids Res. 2008. vol. 36: W411-415.

Fundel et al., RelEx—relation extraction using dependency parse trees. Bioinformatics. 2007. vol. 23 (No. 3): 365-371.

Klein et al., Accurate Unlexicalized Parsing. Proceedings of the 41st Meeting of the Association for Computational Linguistics. Jul. 2003. pp. 423-430.

Marneffe et al., Generating Typed Dependency Parses from Phrase Structure Parses. 2006.

Ding et al., Mining MEDLINE: abstracts, sentences, or phrases?; 2002. pp. 326-337.

Nédellec C. Learning language in logic—genic interaction extraction challenge; 2005. pp. 31-37.

Bell et al., Mixture of logistic models and an ensemble approach for extracting protein-protein interactions. ACM-BCB. 2011: 371-375.

Bunescu et al., Comparative Experiments on Learning Information Extractors for Proteins and their Interactions. Artif Intell Med. Summarization and Information Extraction from Medical Documents. 2005. vol. 33: 139-155.

Pyysalo et al., BioInfer: a corpus for information extraction in the biomedical domain. BMC Bioinformatics. 2007. vol. 8: 50.

Cohen et al., "Getting Started in Text Mining". PLoS Computational Biology. 2008. vol. 4 (Issue 1): e20.

Doms et al., GoPubMed: exploring PubMed with the Gene Ontology. Nucleic Acids Research. 2005. vol. 33: W783-W786: http://nar.oxfordjournals.org/content/33/suppl_2/W783.long.

Joseph et al., "TPX: Biomedical literature search made easy". Bioinformation. 2012. vol. 8 (Issue 12): 578-580.

\* cited by examiner

AUTOMATED EXTRACTION OF BIO-ENTITY RELATIONSHIPS FROM LITERATURE

CROSS-REFERENCE TO RELATED APPLICATIONS

This application is a continuation-in-part of and claims priority to U.S. nonprovisional application Ser. No. 13/854,546, entitled "Automated Extraction of Bio-Entity Relationships from Literature", filed Apr. 1, 2013 by the same inventor, which claims priority to provisional application No. 61/618,217, entitled "Automated Extraction of Bio-Entity Relationships from Literature", filed Mar. 30, 2012 by the same inventor, all of which are incorporated herein by reference.

BACKGROUND OF THE INVENTION

1. Field of the Invention

This invention relates, generally, to text mining. More particularly, it relates to an automated, standardized method of mining text from various literatures, for example extraction of relationships among proteins.

2. Description of the Prior Art

Biological text mining is known in the art [72], and example software applications and companies include GOPUBMED [73], PUBGENE [74], TPX [75], IPA by INGENUITY®, and NETPRO and XTRACTOR by Molecular Connections. Relationships between two terms, keywords or names, constitute a significant part of public knowledge. Much of such information is documented as unstructured text in different places and forms, such as books, articles and online pages. Though some improvements have been made to improve manual annotation, collecting this information from the literature must still be performed manually. This decreases efficiency, increases incidence of error, decreases organization/standardized format, and increases costs of text mining.

A significant part of biological knowledge is centered on relationships among different biological terms including proteins, genes, small molecules, pathways, diseases, and gene ontology (GO) terms (collectively referred to herein as "bio-entities"). Information on bio-entity relationships, such as protein-protein interactions (PPIs), is indispensable for current understanding of the development of drugs and mechanisms of biological processes and complex diseases [1]. Due to the importance of such information, manual annotation has been used to extract information from scientific literature and deposit this information into various databases [2,3,4,5,6,7,8,9,10,11,12,13,14,15,16,17,18,19]. However, manual annotation is quite time- and resource-consuming, and it has become increasingly difficult to keep pace with the ever-increasing publications in biomedical sciences. In recent years, computational methods have been developed to automatically extract molecular interaction information and other bio-entity relationships from the literature, and the software has been used to assist human annotators to build databases [20,21,22,23,24,25,26,27,28,29,30,31,32,33,34,35,36,37,38,39,40,41].

Many computational studies have recently attempted to extract PPIs from published literatures, mostly PubMed abstracts due to their easy access [42,43]. All methods detect PPIs based on some rules (or patterns, templates, etc.) that can be generated by two approaches: (1) specifying them manually [24,43,44,45,46,47,48,49,50,51,52,53,54,55], or (2) computationally inferring/learning them from manually annotated sentences [56,57,58].

Initial efforts of PPI detection were based on simple rules, such as co-occurrence, which assumes that two proteins likely interact with each other if they co-occur in the same sentence/abstract [59,60]. These approaches tend to produce a large number of false positives, and still require significant manual annotations.

Later studies, aiming to reduce the high false positive rate of earlier methods, used manually specified rules. Although such methods sometimes achieved a higher accuracy than co-occurrence methods by extracting cases satisfying the rules, they have low coverage due to missing cases not covered by the limited number of manually specified rules [24,43,44,45,46,47,48,49,50,51,52,53,54,55].

Recently, machine learning based methods [56,57,58] have achieved better performances than other methods in terms of both decreasing false positive rate and increasing the coverage by automatically learning the language rules using annotated texts. Huang [56] used a dynamic programming algorithm, similar to that used in sequence alignment, to extract patterns in sentences tagged by part-of-speech tagger. Kim (2008a,b) used a kernel approach for learning genetic and protein-protein interaction patterns.

Despite extensive studies, current techniques appear to have only achieved partial success on relatively small datasets. Specifically, Park tested their combinatory categorical grammar (CCG) method on 492 sentences and obtained a recall and precision rate of 48% and 80%, respectively [47]. Context-free grammar (CFG) method of Temkin et. al. was tested on 100 randomly selected abstracts and obtained a recall and precision of 63.9% and 70.2%, respectively [46]. Preposition-based parsing method was tested on 50 abstracts with a precision of 70% [52]. A relational parsing method for extracting only inhibition relation was tested on 500 abstracts with a precision and recall of 90% and 57%, respectively [45]. Ono manually specified rules for four interaction verbs (interact, bind, complex, associate), which were tested on 1586 sentences related to yeast and $E.\ coli$, and obtained an average recall and precision of 83.6% and 93.2%, respectively [53]. Huang et al. used a sequence alignment based dynamic programming approach and obtained a recall rate of 80.0% and precision rate of 80.5% on 1200 sentences extracted from online articles [56].

However, a closer analysis of Ono's and Huang's datasets show that they are very biased in terms of the interaction words used. Ono's dataset contains just four interaction words, while in Huang's study, although more verbs were mentioned, the number of sentences containing "interact" and "bind" (and their variants) represents 59.3% of all 1,200 sentences. In Ono's dataset, there is an unrealistic high proportion of true samples (74.7%), making it much easier to obtain good recall and precision. In Huang's study, an arbitrary number of sentences were chosen from 1,200 sentences as training data and the rest as testing data, while some cross validation tests should be used. Kim et al. (2008b) developed a web server, PIE, and tested their method on BioCreative [37,38,61] dataset and achieved very good performance—for PPI article filter task.

Accordingly, given the amount of information produced in digital format every day, what is needed is an automated, accurate, and thorough method of mining bio-entity information from literature as structured form. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for an improved, automated and more efficient text mining procedure is now met by a new, useful and nonobvious invention.

In an embodiment, the current invention comprises computer-implemented software application, the software accessible from a non-transitory, computer-readable media and providing instructions for a computer processor to extract textual relationships or semantic information from non-annotated data by natural language processing and graph theoretic algorithm. The instructions include receiving a plurality of known text strings and interaction words (e.g., dictionaries) and a set of annotated text. The set of annotated text (also called training data), for which the classes (true or false) of the triplets in the text are known, is used to build a training model. The training model can be any decision support tool, for example a decision tree. However, other training models or machine learning methods can also be used since features can be extracted for the triplets from the dependency graphs. The decision support tool has multiple levels, each level having a decision node that is associated with a portion of the classes. Each triplet in the training data is represented at different levels with different levels of details in the decision tree (see FIG. 2). The decision support tool can further be built using other information, such as the relationships among the typed dependencies.

Upon building the decision support tool, the software application receives non-annotated data (e.g., published literatures). A textual clause within the non-annotated data is extracted and includes a triplet containing two targeted words and an interaction word associating the two targeted words to each other. The extracted textual clause is parsed into its grammatical components through the decision support tool based on the components' dependencies on/from one another. The non-annotated texts are parsed in the same way as the annotated texts. The dependencies have a hierarchical structure, and the hierarchical structure include multiple levels. The subordinate levels have a simplified pattern than the level from which they depend. The triplet can be extracted from the textual clause by matching the textual clause to the first level of the hierarchical structure. If they match, the extraction is true, and if they do not match, the extraction is false. If they do not match, the triplet can be extracted from the textual clause by matching the textual clause to the second level of the hierarchical structure. If they match, the extraction is true, and if they do not match, the extraction is false.

A threshold probability value is assigned to each pattern in the training data based on the number of true and false cases associated with the particular pattern.

The textual clause corresponding to the triplet can be tagged with a probability value based on the probability of the pattern in the training data that was matched to the triplet. If the probability value meets the threshold, then the triplet is classified as true. If the probability value fails to meet the threshold, then the triplet is classified as false. This can be done on each level of the hierarchical structure.

The simplified pattern of the second level may be created by replacing non-triplet words with wild cards to permit extraction of non-annotated data that do not contain those non-triplet words.

A third level may be included in the hierarchical structure with a separate decision node and level of detail. The third level would have an even further simplified pattern from the second level. When the textual clause fails to match the second level, the triplet can be extracted from the textual clause by matching the textual clause to the third level of the hierarchical structure. If they match, the extraction is true, and if they do not match, the extraction is false. In a further embodiment, the further simplified pattern can be created by grouping synonyms of the interaction word with the interaction word. This would permit extraction of non-annotated data not containing the exact interaction word but containing one of the synonyms.

The two targeted words can be two bio-entities, such that the interaction word associates the two bio-entities with each other. In a further embodiment, the bio-entities can be two proteins.

The instructions may further include receiving a structured form format that corresponds to the known text strings. When an extracted triplet is classified as true, the triplet can be stored in the structured form format to facilitate retrieval at a future time.

In a separate embodiment, the current invention comprises a computer-implemented method of extracting textual relationships, semantic information (e.g., semantic bio-entity relationships), or patterns from non-annotated language by natural language processing and graph theoretic algorithm. The method includes the steps summarized above.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which.

DETAILED DESCRIPTION OF THE PREFERRED EMBODIMENT

Figure 1:
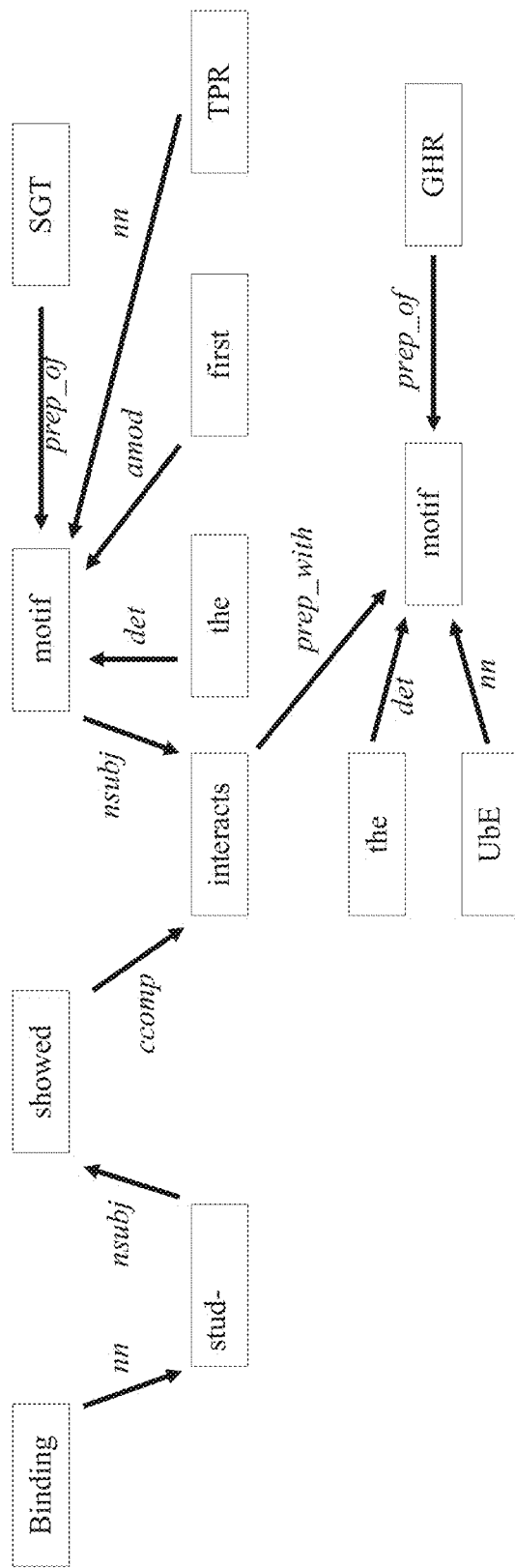
FIG. 1 depicts a grammatical relationship graph for a sentence.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The current invention discloses an automated and standardized software application, system, and method of extracting relationships, for example bio-entity relationships, in text or literature. The invention is illustrated herein by an example of extraction of relationships among proteins. However, it is contemplated that the current invention can be used in various other domains as well to extract relationships within the text. This has various applications, for example building biomedical databases, search engines, knowledge bases, or any other applications that may use organized relationships of content within literatures.

An interaction between two proteins in a sentence is described by at least one and typically only one interaction word, for example "interact", "bind", "phosphorylate", etc. Ideally, one would want to extract not only the names of interacting proteins but also the corresponding interaction words that may describe the type of the interaction [62]. The two protein names and the interaction word are herein referred to as a "PPI triplet". For example, consider the following sentence:

"It is shown here that PAHX interacts with FKBP52, but not with FKBP12, suggesting that it is a specific target of FKBP52."

The foregoing sentence contains four protein names (PAHX, FKBP52, FKBP12, and FKBP52 (the second occurrence of FKBP52 in the sentence)) and one interaction word ("interacts"). In total, there are five triplets: (1) PAHX-interacts-FKBP52, (2) PAHX-interacts-FKBP12, (3) PAHX-interacts-FKBP52 (second FKBP52), (4) interacts-FKBP52-FKBP12, and (5) interacts-FKBP12-FKBP52 (second FKBP52), where FKBP52-interacts-FKBP52 is not counted. These five triplets have only one true interaction: PAHX-interacts-FKBP52. This example of the current invention describes a novel method for extracting the triplets from sentences and classifying them as true or false with probability values based on whether the interaction word correctly describes the interaction relationship between the two protein names. Thus, a threshold probability value should be established. If the probability values assigned to the triplets meet the threshold, the triplet is classified as true. If the probability values assigned to the triplets fail to meet the threshold, the triplet is classified as false.

Relationships between two terms or names constitute a significant part of current knowledge. Much of such information is documented as unstructured text in different places, such as books, articles and online pages. Automatic extraction of such information allows the information to be stored in structured form so that it can be easily and accurately retrieved when needed.

In an embodiment, the current invention includes a novel approach to automatically extracting such information from raw text based on natural language processing (NLP) and graph theoretic algorithm. For example, this method may be used to automatically extract protein-protein relationships in biomedical literature and obtain better performance than conventional methodologies.

This method can be used to extract many types of relationship information, which can be useful for multiple purposes. For example, in biomedical research, relationships involving terms, such as proteins, gene, pathways, diseases and drugs, can be very useful and valuable for biomedical and pharmaceutical research. Relationships among people can be important in social studies and practices as well. In general, it can be used to automatically build the knowledge base for various types of important information from texts in digital form. It can also be useful for building search engines for highly specific and accurate information retrieval.

Method

To extract triplets from sentences, dictionaries were used for protein names and for interaction words (e.g., interact, contact, associate, etc.).

The novel approach uses natural language processing (NLP) techniques and graph theoretical algorithm. There have been few methods that have used NLP techniques in protein-protein interaction extraction in the past [35,63,64]. Sentences were initially parsed using Stanford sentence parser [65,66], and the dependencies (i.e., grammatical relations) were obtained among the words in the sentences.

For example, consider the following sentence:

"Binding studies showed that the first TPR motif of SGT interacts with the UbE motif of the GHR."

This sentence can be parsed according to FIG. 1 representing the grammatical relationships between the words in the sentence.

The words/relationships in FIG. 1 are typed dependencies as defined in Marneffe et al. [66], which is incorporated herein by reference. The typed dependencies have a hierarchical structure themselves. At the top level is "dep" (dependent), which has the following types: "aux" (auxiliary), "arg" (argument), "cc" (coordination), "conj" (conjunct), "expl" (expletive), "mod" (modifier), "parataxis" (parataxis), "punct" (punctuation), "ref" (referent) and "sdep" (semantic dependent). Each of these types can have subtypes. For example, "arg" (argument) can have "agent" (agent), "comp" (complement) and "subj" (subject), where "subj" has "nsubj" (nominal subject) and "csubj" (clausal subject). From the graph of FIG. 1, a sub-graph can be extracted containing the triplet (i.e., two protein names and the interaction word). To do so, the three pairwise shortest paths between pairs of the triplet elements were determined. This provided the sub-graph, called grammatical relationship graph for triplets (GRGT), as depicted in FIG. 2A.

Figure 2A:
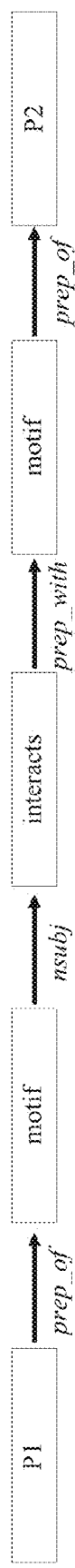
FIG. 2A depicts a grammatical relationship graph for triplet word strings and non-triple word strings on the first level, wherein P1 is the first protein and P2 is the second protein.

The GRGT of FIG. 2A describes the extraction of the phrasing,

"motif of P1 (SGT) interacts with motif of P2 (GHR)".

This graph allows the inference of the interaction between SGT and GHR. This can be applied to the majority of the triplets and their corresponding GRGT. A new triplet that matches the above pattern can be classified as true. Given a set of manually annotated triplets, a pattern matching approach can be used to classify new triplets. Since the directionality information for the true patterns can also be annotated, the direction can also be inferred at the same time.

To account for similar but not exact matches, a simple decision tree was designed. The simple decision tree has one decision node at each level, representing the patterns at different level of details. Using the above interaction as an example, the first level of the decision tree would be the pattern as depicted in FIG. 2A.

Figure 2B:
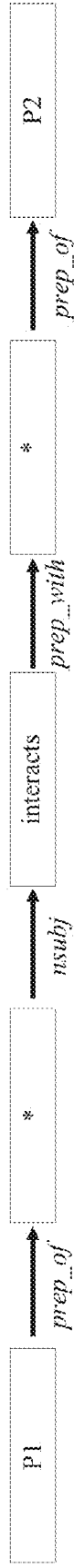
FIG. 2B depicts a grammatical relationship graph for triplet word strings on the second level, wherein P1 is the first protein, P2 is the second protein, and the non-triplet word strings have been replaced by a wildcard.

At the second level is a simplified pattern by replacing all the other words except the triplet words with a wildcard ("*") as depicted in FIG. 2B. At this level, consider the following sentence:

"C-terminal domain of protein A interacts with residue 30-50 of protein B."

The foregoing sentence would be a match to the GRGT seen in FIG. 2B with the wildcards substituted for any non-triplet word.

Figure 2C:
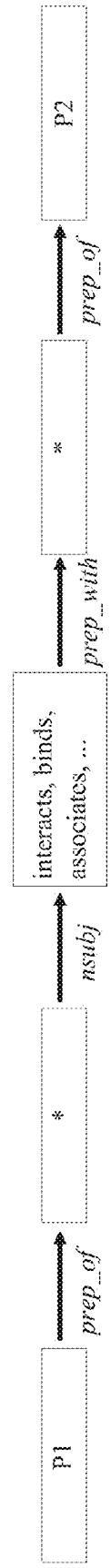
FIG. 2C depicts a grammatical relationship graph for triplet word strings on the third level, wherein P1 is the first protein, P2 is the second protein, and the interaction word includes various synonyms of the original interaction word.

At the third level, depicted in FIG. 2C, similar interaction words are grouped together. For example, "interacts, "binds" and "associates" can be in one group. For example, as used in a study during development of the methodology, all the interaction words in the interaction word dictionary can be manually grouped into twenty groups according to their grammatical similarity. In the study, this provided a standard for comparison of results to the conventional art, which is described infra.

If a triplet cannot be matched to any patterns at the first level, it will be matched with those at the second level. If a triplet cannot be matched to any patterns at the second level, it will be matched with those at the third level, and so on. With reduced representation, some patterns will have both true and false cases. When a triplet is matched to a pattern, the probability of the triplet being true can be assigned as the proportion of true cases with that pattern, as in a standard classification tree. If a triplet cannot be matched with any existing pattern, then it will be classified as false.

Comparison to the Conventional Art

The method of the current invention was compared to the best performing method as provided in the prior art by Bui et al. [35] on several benchmark datasets, as depicted in Table 1.

TABLE 1

Performance comparison of our method using GRGT with Bui et. al. on four benchmark datasets.

| | HPRD50[64] | | | IEPA[67] | | | LLL[68] | | | PICAD[69] | | |
|---|---|---|---|---|---|---|---|---|---|---|---|---|
| | F | P | R | F | P | R | F | P | R | F | P | R |
| Bui et. al. | 71.7 | 62.2 | 84.7 | 73.4 | 62.9 | 88.1 | 83.6 | 81.9 | 85.4 | — | — | — |
| GRGT | 77.9 | 92.2 | 67.5 | 74.4 | 89.7 | 63.6 | 84.2 | 92.8 | 77.1 | 77.3 | 92.7 | 66.3 |

F: F- measure,
P: precision,
R: recall.

The novel method of the current invention achieved better F-measures for all the benchmark applicable datasets. Most of the cases misclassified are true triplets that cannot be matched with any known patterns. It is worth mentioning that the precision of the current method is higher than that of Bui's, which is important in text mining since false positives are so often a troublesome issue. Normally, one can tolerate more of lower recall rate since interactions often occur more than once in literature. As long as one of them is classified as true, the interaction can be extracted.

According to the present invention, patterns can be simplified so that more true triplets can be matched if they are similar to true patterns, but not exactly the same. An option is to use the hierarchical structure of the typed dependencies. For example, nsubj (nominal subject) can be reduced to subj (subject) or even further to arg (argument). By simplification, recall is improved, but the precision may be sacrificed. Recall and precision should be balanced to achieve optimal performance.

To further improve the performance, one can annotate more interaction cases to increase the training set, which would improve the recall rate of the present method. More than two million triplets enriched with true cases, using a substantially similar procedure as described supra, were utilized and parsed into patterns at several representation levels. Results showed 2,236 patterns with occurrences more than 100 times, which accounted for nearly a half-million triplets. It appears that the number of common patterns that authors use to describe molecular interactions is limited, and they are repeatedly used over time. Most of the rare patterns are likely false cases. The frequently-seen patterns in the two million triplets may have included most of the true patterns authors use to describe protein-protein interactions. Of course, some frequent patterns can be false as well.

Exact patterns can be further reduced and different decision trees can be developed to achieve better performance. Additionally, it is contemplated by the current invention that when directionality is relevant, the directions of the interactions can be annotated. This can enhance the current methodology's development of accurate molecular interaction extraction.

Application of Software

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

Aspects of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

EXAMPLE

Figure 3:
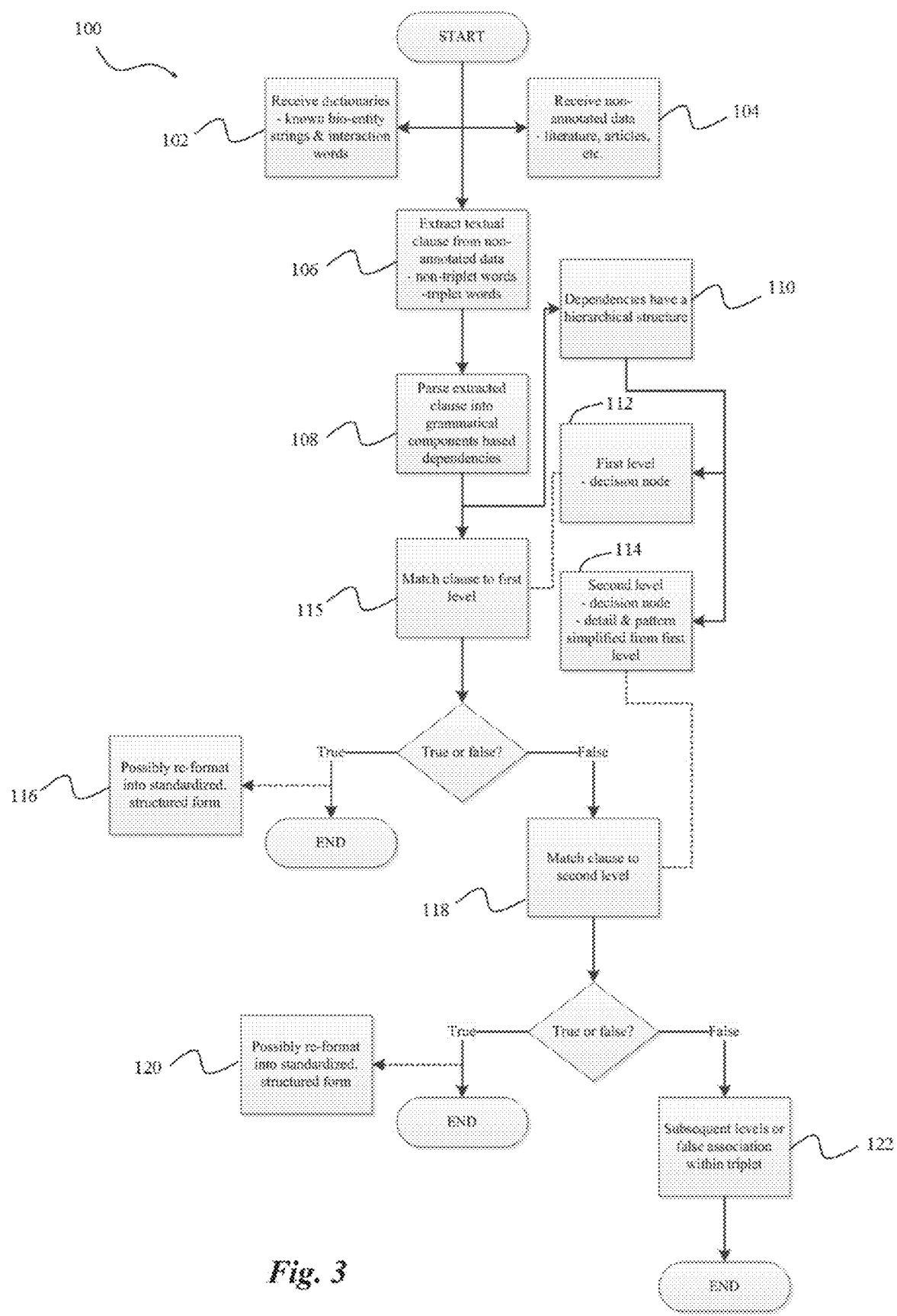
FIG. 3 is a flowchart depicting the steps as disclosed in embodiment of the current invention.

FIG. 3 is a step-by-step flowchart 100 of an embodiment of the current invention as it may be implemented onto a software application. A plurality of known textual (e.g., bio-entity) strings and interaction words received 102 by the software application, as is annotated data containing known true and false patterns/classes 110 used as a training set. A decision support tool (e.g., decision tree) is automatically built based on the annotated patterns/classes 111. The decision support tool has a first level 112 and a second level 114, each level having a decision node and level of detail. The second level has a pattern that is simplified compared to the first level 114.

Non-annotated data (e.g., literature, articles, etc.) is received 104. One or more textual clauses are then extracted from the non-annotated data 106, said textual clause including non-triplet words and triplet words. Subsequently, the extracted clause is parsed through the decision support tool into its grammatical component based on its dependencies 108.

After the extracted clause has been parsed into its components, an attempt is made to match the clause to the first level 115. If a match is made, the triplet can be extracted from the clause and the interaction may be deemed as true. If true, the extracted triplet may be re-formatted into a standardized, structured form 116 for easier retrieval at a future time.

If a match is not made and is deemed false, the extracted clause moves onto the second level, and an attempt is made to match the clause to the second level 118. If a match is made, the triplet can be extracted from the clause and the interaction may be deemed as true. If true, the extracted triplet may be re-formatted into a standardized, structured form 120 for easier retrieval at a future time. If a match is not made and is deemed false, the extracted clause may move onto subsequent levels or be deemed an entirely false interaction 122.

REFERENCES

The following references are hereby collectively incorporated by reference to the same extent as if they were individually incorporated by reference.

1. Kann M G (2007) Protein interactions and disease: computational approaches to uncover the etiology of diseases. Brief Bioinform 8: 333-346.
2. Keshava Prasad T S, Goel R, Kandasamy K, Keerthikumar S, Kumar S, et al. (2009) Human Protein Reference Database—2009 update. Nucleic Acids Res 37: D767-772.
3. Salwinski L, Miller C S, Smith A J, Pettit F K, Bowie J U, et al. (2004) The Database of Interacting Proteins: 2004 update. Nucleic Acids Res 32: D449-451.
4. Chatr-aryamontri A, Ceol A, Palazzi L M, Nardelli G, Schneider M V, et al. (2007) MINT: the Molecular INTeraction database. Nucleic Acids Res 35: D572-574.
5. Stark C, Breitkreutz B J, Reguly T, Boucher L, Breitkreutz A, et al. (2006) BioGRID: a general repository for interaction datasets. Nucleic Acids Res 34: D535-539.
6. Mishra G R, Suresh M, Kumaran K, Kannabiran N, Suresh S, et al. (2006) Human protein reference database—2006 update. Nucleic Acids Res 34: D411-414.
7. Pagel P, Kovac S, Oesterheld M, Brauner B, Dunger-Kaltenbach I, et al. (2005) The MIPS mammalian protein-protein interaction database. Bioinformatics 21: 832-834.
8. Beuming T, Skrabanek L, Niv M Y, Mukherjee P, Weinstein H (2005) PDZBase: a protein-protein interaction database for PDZ-domains. Bioinformatics 21: 827-828.
9. Alfarano C, Andrade C E, Anthony K, Bahroos N, Bajec M, et al. (2005) The Biomolecular Interaction Network Database and related tools 2005 update. Nucleic Acids Res 33: D418-424.
10. Mathivanan S, Periaswamy B, Gandhi TKB, Kandasamy K, Suresh S, et al. (2006) An evaluation of human protein-protein interaction data in the public domain. BMC Bioinformatics 7: S19.
11. Aranda B, Achuthan P, Alam-Faruque Y, Armean I, Bridge A, et al. (2009) The IntAct molecular interaction database in 2010. Nucleic Acids Res 38: D525-531.
12. Han K, Park B, Kim H, Hong J, Park J (2004) HPID: the Human Protein Interaction Database. Bioinformatics 20: 2466-2470.
13. Kuhn M, von Mering C, Campillos M, Jensen L J, Bork P (2008) STITCH: interaction networks of chemicals and proteins. Nucleic Acids Res 36: D684-688.
14. Griffith O L, Montgomery S B, Bernier B, Chu B, Kasaian K, et al. (2008) ORegAnno: an open-access community-driven resource for regulatory annotation. Nucleic Acids Res 36: D107-113.

15. Gama-Castro S, Jimenez-Jacinto V, Peralta-Gil M, Santos-Zavaleta A, Penaloza-Spinola M I, et al. (2008) RegulonDB (version 6.0): gene regulation model of *Escherichia coli* K-12 beyond transcription, active (experimental) annotated promoters and Textpresso navigation. Nucleic Acids Res 36: D120-124.

16. Grote A, Klein J, Retter I, Haddad I, Behling S, et al. (2009) PRODORIC (release 2009): a database and tool platform for the analysis of gene regulation in prokaryotes. Nucleic Acids Res 37: D61-65.

17. Shahi P, Loukianiouk S, Bohne-Lang A, Kenzelmann M, Kuffer S, et al. (2006) Argonaute—a database for gene regulation by mammalian microRNAs. Nucleic Acids Res 34: D115-118.

18. Sierro N, Kusakabe T, Park K J, Yamashita R, Kinoshita K, et al. (2006) DBTGR: a database of tunicate promoters and their regulatory elements. Nucleic Acids Res 34: D552-555.

19. Matys V, Fricke E, Geffers R, Gossling E, Haubrock M, et al. (2003) TRANSFAC: transcriptional regulation, from patterns to profiles. Nucleic Acids Res 31: 374-378.

20. Korbel J O, Doerks T, Jensen L J, Perez-Iratxeta C, Kaczanowski S, et al. (2005) Systematic association of genes to phenotypes by genome and literature mining. PLoS Biol 3: e134.

21. Koike A, Niwa Y, Takagi T (2005) Automatic extraction of gene/protein biological functions from biomedical text. Bioinformatics 21: 1227-1236.

22. Chowdhary R, Zhang J, Liu J S (2009) Bayesian inference of protein-protein interactions from biological literature. Bioinformatics 25: 1536-1542.

23. Rzhetsky A, Seringhaus M, Gerstein M (2008) Seeking a new biology through text mining. Cell 134: 9-13.

24. Jensen L J, Saric J, Bork P (2006) Literature mining for the biologist: from information retrieval to biological discovery. Nat Rev Genet 7: 119-129.

25. Gonzalez G, Uribe J C, Tari L, Brophy C, Baral C (2007) Mining gene-disease relationships from biomedical literature: weighting protein-protein interactions and connectivity measures. Pac Symp Biocomput: 28-39.

26. Huang M, Ding S, Wang H, Zhu X (2008) Mining physical protein-protein interactions from the literature. Genome Biol 9 Suppl 2: S12.

27. Barrell D, Dimmer E, Huntley R P, Binns D, O'Donovan C, et al. (2009) The GOA database in 2009—an integrated Gene Ontology Annotation resource. Nucleic Acids Res 37: D396-403.

28. Ceol A, Chatr-Aryamontri A, Licata L, Cesareni G (2008) Linking entries in protein interaction database to structured text: the FEBS Letters experiment. FEBS Lett 582: 1171-1177.

29. Mottaz A, Yip Y L, Ruch P, Veuthey A L (2008) Mapping proteins to disease terminologies: from UniProt to MeSH. BMC Bioinformatics 9 Suppl 5: S3.

30. Wong L S, Liu G M (2010) Protein Interactome Analysis for Countering Pathogen Drug Resistance. Journal of Computer Science and Technology 25: 124-130.

31. Tikk D, Thomas P, Palaga P, Hakenberg J, Leser U (2010) A Comprehensive Benchmark of Kernel Methods to Extract Protein-Protein Interactions from Literature. PLoS Computational Biology 6: e1000837.

32. Kano Y, Nguyen N, Saetre R, Yoshida K, Miyao Y, et al. (2008) Filling the gaps between tools and users: a tool comparator, using protein-protein interaction as an example. Pac Symp Biocomput: 616-627.

33. Iossifov I, Rodriguez-Esteban R, Mayzus I, Millen K J, Rzhetsky A (2009) Looking at Cerebellar Malformations through Text-Mined Interactomes of Mice and Humans. Plos Computational Biology 5: -.

34. Bui Q C, Nuallain B O, Boucher C A, Sloot P M A (2010) Extracting causal relations on HIV drug resistance from literature. BMC Bioinformatics 11: 101.

35. Bui Q C, Katrenko S, Sloot P M (2010) A hybrid approach to extract protein-protein interactions. Bioinformatics.

36. Pyysalo S, Airola A, Heimonen J, Bjorne J, Ginter F, et al. (2008) Comparative analysis of five protein-protein interaction corpora. BMC Bioinformatics 9 Suppl 3: S6.

37. Krallinger M, Valencia A (2007) Assessment of the second BioCreative PPI task: automatic extraction of protein-protein interactions. Proceedings of the BioCreative Workshop: 41-54.

38. Krallinger M, Leitner F, Rodriguez-Penagos C, Valencia A (2008) Overview of the protein-protein interaction annotation extraction task of BioCreative II. Genome Biol 9 Suppl 2: S4.

39. Hu X, Zhang X, Yoo I, Wang X, Feng J (2010) Mining Hidden Connections among Biomedical Concepts from Disjoint Biomedical Literature Sets through Semantic-based Association Rule. International Journal of Intelligent System 25: 207-223.

40. Hu X, Wu D (2007) Data Mining and Predictive Modeling of Biomolecular Network from Biomedical Literature Databases. IEEE/ACM Transactions on Computational Biology and Bioinformatics: 251-263.

41. Giles C B, Wren J D (2008) Large-scale directional relationship extraction and resolution. BMC Bioinformatics 9 Suppl 9: S11.

42. Skusa A, Ruegg A, Kohler J (2005) Extraction of biological interaction networks from scientific literature. Brief Bioinform 6: 263-276.

43. C Blaschke, M A Andrade, C Ouzounis, Valencia A (1999) Automatic extraction of biological information from scientific text: protein-protein interactions. Proc Int Conf Intell Syst Mol Biol: 60-67.

44. Ng S K, Wong M (1999) Toward Routine Automatic Pathway Discovery from On-line Scientific Text Abstracts. Genome Inform Ser Workshop Genome Inform 10: 104-112.

45. J Pustejovsky, J Castano, J Zhang, M Kotecki, Cochran B (2002) Robust relational parsing over biomedical literature: extracting inhibit relations. Pac Symp Biocomput: 362-373.

46. J M Temkin, Gilder M R (2003) Extraction of protein interaction information from unstructured text using a context-free grammar. Bioinformatics 19: 2046-2053.

47. J C Park, H S Kim, Kim J J (2001) Bidirectional incremental parsing for automatic pathway identification with combinatory categorial grammar. Pac Symp Biocomput: 396-407.

48. J Thomas, D Milward, C Ouzounis, S Pulman, Carroll M (2000) Automatic extraction of protein interactions from scientific abstracts. Pac Symp Biocomput: 541-552.

49. Saric J, Jensen L J, Ouzounova R, Rojas I, Bork P (2006) Extraction of regulatory gene/protein networks from Medline. Bioinformatics 22: 645-650.

50. A Yakushiji, Y Tateisi, Y Miyao, Tsujii J (2001) Event extraction from biomedical papers using a full parser. Pac Symp Biocomput 408-19.

51. C Friedman, P Kra, H Yu, M Krauthammer, Rzhetsky A (2001) GENIES: a natural-language processing system for the extraction of molecular pathways from journal articles. Bioinformatics 17: S74-82.

52. G Leroy, Chen H (2002) Filling preposition-based templates to capture information from medical abstracts. Pac Symp Biocomput: 350-361.

53. T Ono, H Hishigaki, A Tanigami, Takagi T (2001) Automated extraction of information on protein-protein interactions from the biological literature. Bioinformatics 17: 155-161.

54. Wong L (2001) PIES, a protein interaction extraction system. Pac Symp Biocomput: 520-531.

55. Narayanaswamy M, Ravikumar K E, Vijay-Shanker K (2005) Beyond the clause: extraction of phosphorylation information from medline abstracts. Bioinformatics 21 Suppl 1: i319-327.

56. M Huang, X Zhu, Y Hao, D G Payan, K Qu, et al. (2004) Discovering patterns to extract protein-protein interactions from full texts. Bioinformatics: 3604-3612.

57. Kim S, Yoon J, Yang J (2008) Kernel approaches for genic interaction extraction. Bioinformatics 24: 118-126.

58. Malik R, Franke L, Siebes A (2006) Combination of text-mining algorithms increases the performance. Bioinformatics 22: 2151-2157.

59. Jenssen T K, Laegreid A, Komorowski J, Hovig E (2001) A literature network of human genes for high-throughput analysis of gene expression. Nat Genet 28: 21-28.

60. Stapley B J, Benoit G (2000) Biobibliometrics: information retrieval and visualization from co-occurrences of gene names in Medline abstracts. Pac Symp Biocomput: 529-540.

61. Krallinger M, Morgan A, Smith L, Leitner F, Tanabe L, et al. (2008) Evaluation of text-mining systems for biology: overview of the Second BioCreative community challenge. Genome Biol 9 Suppl 2: S1.

62. Hatzivassiloglou V, Weng W (2002) Learning anchor verbs for biological interaction patterns from published text articles. Int J Med Inform 67: 19-32.

63. Kim S, Shin S Y, Lee I H, Kim S J, Sriram R, et al. (2008) PIE: an online prediction system for protein-protein interactions from text. Nucleic Acids Res 36: W411-415.

64. Fundel K, Kuffner R, Zimmer R (2007) RelEx—relation extraction using dependency parse trees. Bioinformatics 23: 365-371.

65. Klein D, Manning C D (2003) Accurate Unlexicalized Parsing. Proceedings of the 41st Meeting of the Association for Computational Linguistics. pp. 423-430.

66. Marneffe M-Cd, MacCartney B, Manning C D. Generating Typed Dependency Parses from Phrase Structure Parses.; 2006.

67. Ding J, Berleant D, Nettleton D, Wurtele E. Mining MEDLINE: abstracts, sentences, or phrases; 2002. pp. 326-337.

68. Nédellec C. Learning language in logic—genic interaction extraction challenge; 2005. pp. 31-37.

69. Bell L, Zhang J, Niu X (2011) Mixture of logistic models and an ensemble approach for extracting protein-protein interactions. ACM-BCB: 371-375.

70. Bunescu R, Ge R, Kate R, Marcotte E, Mooney R, et al. (2005) Comparative Experiments on Learning Information Extractors for Proteins and their Interactions. Artif Intell Med, Summarization and Information Extraction from Medical Documents 33: 139-155.

71. Pyysalo S, Ginter F, Heimonen J, Bjorne J, Boberg J, et al. (2007) BioInfer: a corpus for information extraction in the biomedical domain. BMC Bioinformatics 8: 50.

72. K. Bretonnel Cohen & Lawrence Hunter (January 2008). "Getting Started in Text Mining". PLoS Computational Biology 4 (1): e20.

73. GoPubMed: exploring PubMed with the Gene Ontology, A. Doms and M. Schroeder, 2005, http://nar.oxfordjournals.org/content/33/suppl_2/W783.long.

74. Tor-Kristian Jenssen, Astrid Lægreid, Jan Komorowskil & Eivind Hovig (2001). "A literature network of human genes for high-throughput analysis of gene expression". Nature Genetics 28 (1): 21-28.

75. Thomas Joseph, Vangala G Saipradeep, Ganesh Sekar Venkat Raghavan, Rajgopal Srinivasan, Aditya Rao, Sujatha Kotte & Naveen Sivadasan (2012). "TPX: Biomedical literature search made easy". Bioinformation 8 (12): 578-580.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

DEFINITIONS OF CLAIM TERMS

Accurate interaction: This term is used herein to refer to a true association between two targeted words (e.g., two bio-entity word strings) and their corresponding interaction word.

Analogous interaction word: This term is used herein to refer to synonyms of the original interaction word to provide a broader set of interaction words in the triplets that can be captured.

Annotated text: This term is used herein to refer to any literature, or portion thereof, that has been previously parsed or annotated to determine relationships and semantic information from the text contained within said literature. For example, literature that has been annotated can provide patterns of associations between bio-entities or other text.

Component: This term is used herein to refer to a constituent part of the overall independent or dependent clause being analyzed by the current methodology.

Decision node: This term is used herein to refer to a representation of a decision regarding the accurateness (i.e., true/false) of a match between the targeted textual clause and the level to which the clause is being compared.

Decision support tool: This term is used herein to refer to a computer-based information system that supports organizational and automated decision-making activities. The decision support tool uses useful information to analyze possible decisions and influences and choose the appropriate decision/solution from its analyses. An example of a decision support tool is a decision tree, though other machine learning methods are contemplated by the current invention.

Dependency: This term is used herein to refer to the grammatical relationship among the components of an independent or dependent clause.

False: This term is used herein to refer to inaccurate match between the textual clause and the level to which the clause is being compared. If the match is deemed false, the clause can automatically be moved along to the next level.

Hierarchical structure: This term is used herein to refer to an organizational structure where the grammatical terms describing the components within a textual clause have subordinates and/or are related to one another.

Interaction word string: This term is used herein to refer to a linear sequence of alphabetic characters that associates two textual strings to one another. For example, in the phrase "protein A interacts with protein B", the term "interacts" is the interaction word, as is the term "does not interact" in the phrase "protein A does not interact with protein B".

Known bio-entity string: This term is used herein to refer to a linear sequence of alphanumeric and symbol characters that discloses a single known biological entity (e.g., molecules, animals, proteins, etc.).

Known textual string: This term is used herein to refer to a linear sequence of alphanumeric and symbol characters that discloses a single known entity (e.g., an individual, a protein, a thing, etc.).

Level of detail: This term is used herein to refer to the grammatical and linguistic structure needed for a textual clause to be captured and extracted.

Level: This term is used herein to refer to a phase representing the level of detail required for capturing textual clauses for annotation or text mining. For example, the current methodology can have multiple levels, such that the current methodology can not only capture textual clauses that are identical to each other and what is known, but also capture textual clauses that are not identical to each other and what is known. For example, using the phrase "protein A interacts with protein B", the identical phrase "protein A interacts with protein B" can be captured on one level, and the similar phrase "protein A corresponds to protein B" can also be captured on another level.

Non-annotated data: This term is used herein to refer to any literature, or portion thereof, that has not undergone the current methodology of text mining to determine semantic information from text contained within said literature. For example, non-annotated data can include a published scientific article.

Non-triplet word string: This term is used herein to refer to any words within non-annotated data that are not the targeted words desired for obtaining semantic information or relationships.

Probability value: This term is used herein to refer to a percentage chance of a set of two targeted words having true association with a corresponding interaction word within a particular level.

Semantic bio-entity relationship: This term is used herein to refer to a whole or partial linguistic association or link between two or more biological entities (e.g., molecules, animals, proteins, etc.). For example, the phrase "protein A interacts with protein B" shows a semantic relationship between protein A and protein B, as does the phrase "protein A does not interact with protein B".

Simplified pattern: This term is used herein to refer to the level of detail required for a targeted textual clause to meet in order to produce a true match, as that textual clause moves from the first level to the second level and so on. A pattern becomes more simplified as the level of the detail is reduced/broadened so as to capture more textual clauses or triplets.

Structured form format: This term is used herein to refer to a standardized format in which extracted triplets can be structured for easier retrieval at a future time. When a triplet is extracted (i.e., it has been determined to be true), the triplet automatically uses the structured form format for storage.

Textual clause: This term is used herein to refer to a dependent or independent clause within non-annotated data (e.g., scientific article).

Textual relationship or semantic information: These terms are used herein to refer to a whole or partial linguistic association or link between two or more word entities (e.g., historical figures, pharmaceutical drugs and side effects, bio-entities, etc.). For example, the phrase "drug X causes Y" shows a textual relationship and provides semantic information about drug X and effect Y, as does the phrase "drug X does not cause Y".

Threshold probability value: This term is used herein to refer to a minimum percentage chance that two targeted words have a true association with a corresponding interaction word within a particular level. A triplet should meet this threshold probability in order to be extracted from the textual clause.

Training data: This term is used herein to refer to information derived from annotated text and used to build a decision support system that aids in the annotation of non-annotated literature.

Triplet: This term is used herein to refer to any words that are targeted for obtaining semantic information or relationships, along with words used for associating the targeted words to each other. A triplet would typically include two targeted words (e.g., bio-entities) and an interaction word that associates the targeted words.

True: This term is used herein to refer to an accurate match between the textual clause and the level to which the clause is being compared.

Wildcard: This term is used herein to refer to a symbol used to represent the presence of unspecified characters or words. Replacing certain word strings (typically non-triplet words) with wildcards broaden or simplify the pattern by not rejecting words in the wildcard position.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. One or more non-transitory, tangible computer-readable media having computer-executable instructions for performing a method by running a software program on a computer, the computer operating under an operating system, the method including issuing instructions from the software program to extract semantic bio-entity relationships or patterns from non-annotated data by natural language processing and graph theoretic algorithm, the instructions comprising:
   receiving a plurality of known bio-entity strings and a plurality of interaction word strings;
   receiving annotated text as training data that contains true and false patterns;
   automatically building a decision support tool based on said true and false patterns to which said non-annotated data can be parsed,
   said decision support tool including at least a first level and a second level, said first level having a first decision node, said second level having a second decision node, said first and second decision nodes each associated with at least a portion of said true and false patterns;
   receiving said non-annotated data;
   extracting a textual clause of said non-annotated data that contains non-triplet word strings and at least one triplet, said at least one triplet including a first bio-entity, a second bio-entity, and an interaction word, wherein said interaction word indicates a possible relationship between said first bio-entity and said second bio-entity;

automatically parsing said extracted textual clause through said decision support tool to obtain a plurality of components based on dependencies among said plurality of components;

extracting said at least one triplet from said plurality of components by attempting to match said plurality of components of said parsed, extracted textual clause to said first level of said decision support tool;

identifying extraction of said at least one triplet as true if said plurality of components matches said first level of said decision support tool;

identifying extraction of said at least one triplet as false if said plurality of components fails to match said first level of said decision support tool;

as a result of said plurality of components failing to match said first level of said decision support tool, extracting said at least one triplet from said plurality of components by attempting to match said plurality of components to said second level of said decision support tool;

identifying extraction of said at least one triplet as true if said plurality of components matches said second level of said decision support tool, said second level of said decision support tool being a simplified pattern of said first level of said decision support tool to capture textual clauses that are not identical to said extracted textual clause; and identifying extraction of said at least one triplet as false if said plurality of components fails to match said second level of said decision support tool.

2. One or more non-transitory, tangible computer-readable media as in claim 1, further comprising instructions for:
establishing a threshold probability value based on probable accuracy retrieved from said decision support tool;
said step of extracting said at least one triplet from said extracted textual clause by attempting to match said extracted textual clause to said first level, including:
tagging said extracted textual clause with a first probability value based on said accurate interaction between said extracted first and second bio-entities and said extracted interaction word within said first level;
classifying said at least one triplet as true as a result of said first probability value meeting said threshold probability value, and
classifying said at least one triplet as false as a result of said first probability value failing to meet said threshold probability value;
said step of extracting said at least one triplet from said extracted textual clause by attempting to match said extracted textual clause to said second level, including:
tagging said extracted textual clause with a second probability value based on said accurate interaction between said extracted first and second bio-entities and said extracted interaction word within said second level;
classifying said at least one triplet as true as a result of said second probability value meeting said threshold probability value, and
classifying said at least one triplet as false as a result of said second probability value failing to meet said threshold probability value.

3. One or more non-transitory, tangible computer-readable media as in claim 1, further comprising instructions for:
receiving a structured form format corresponding to said plurality of known bio-entity strings; and
storing said at least one extracted triplet in said structured form format as a result of a classification of said at least one extracted triplet being true, said storing facilitating retrieval of said at least one extracted, true triplet.

4. One or more non-transitory, tangible computer-readable media as in claim 1, further comprising:
said simplified pattern of said second level automatically created by replacing said non-triplet word strings with a wildcard that permits extraction of non-annotated data not containing said non-triplet word strings.

5. One or more non-transitory, tangible computer-readable media as in claim 1, further comprising instructions for:
establishing a third level in said hierarchical structure, said third level having a third decision node,
said third level being a further simplified pattern of said second level to capture triplets that are not identical to said at least one extracted triplet; and
as a result of said extracted textual clause failing to match said second level, extracting said at least one triplet from said extracted textual clause by attempting to match said extracted textual clause to said third level;
identifying extraction of said at least one triplet as true if said extracted textual clause matches said third level; and
identifying extraction of said at least one triplet as false if said extracted textual clause fails to match said third level.

6. One or more non-transitory, tangible computer-readable media as in claim 5, further comprising:
said further simplified pattern of said third level automatically created by grouping analogous interaction words with said interaction word to permit extraction of non-annotated data not containing said interaction word but containing one of said analogous interaction words.

7. One or more non-transitory, tangible computer-readable media as in claim 1, further comprising:
said first bio-entity being a first protein,
said second bio-entity being a second protein, and
said interaction word associating said first protein to said second protein.

8. One or more non-transitory, tangible computer-readable media as in claim 1, further comprising:
said decision support tool being a decision tree.

9. One or more non-transitory, tangible computer-readable media as in claim 1, further comprising:
the step of automatically building said decision support tool further based on relationships among additional dependencies among said true and false patterns in said annotated data.

10. A computer-implemented method of extracting semantic bio-entity relationships or patterns front non-annotated data by natural language processing and graph theoretic algorithm, comprising the steps of:
receiving a plurality of known bio-entity strings and a plurality of interaction word strings;
receiving annotated text as training data that contains true and false patterns;
automatically building a decision support tool based on said true and false patterns to which said non-annotated data can be parsed,
said decision support tool including at least a first level and a second level, said first level having a first decision node, said second level having a second decision node, said first and second decision nodes each associated with at least a portion of said true and false patterns;
receiving said non-annotated data,
extracting a textual clause of said non-annotated data that contains non-triplet word strings and at least one triplet, said at least one triplet including a first bio-entity, a second bio-entity, and an interaction word, wherein said interaction word indicates a possible relationship between said first bio-entity and said second bio-entity;

automatically parsing said extracted textual clause through said decision support tool to obtain a plurality of components based on dependencies among said plurality of components;

extracting said at least one triplet from said plurality of components by attempting to match said plurality of components of said parsed, extracted textual clause to said first level of said decision support tool;

identifying extraction of said at least one triplet as true if said plurality of components matches said first level of said decision support tool;

identifying extraction of said at least one triplet as false if said plurality of components fails to match said first level of said decision support tool;

as a result of said plurality of components failing to match said first level of said decision support tool, extracting said at least one triplet from said plurality of components by attempting to match said plurality of components to said second level of said decision support tool;

identifying extraction of said at least one triplet as true if said plurality of components matches said second level of said decision support tool, said second level of said decision support tool being a simplified pattern of said first level of said decision support tool to capture textual clauses that are not identical to said extracted textual clause; and identifying extraction of said at least one triplet as false if said plurality of components fails to match said second level of said decision support tool.

11. A computer-implemented method as in claim 10, further comprising instructions for:
establishing a threshold probability value based on probable accuracy retrieved from said decision support tool;
said step of extracting said at least one triplet from said extracted textual clause by attempting to match said extracted textual clause to said first level, including:
tagging said extracted textual clause with a first probability value based on said accurate interaction between said extracted first and second bio-entities and said extracted interaction word within said first level;
classifying said at least one triplet as true as a result of said first probability value meeting said threshold probability value, and
classifying said at least one triplet as false as a result of said first probability value failing to meet said threshold probability value;
said step of extracting said at least one triplet from said extracted textual clause by attempting to match said extracted textual clause to said second level, including:
tagging said extracted textual clause with a second probability value based on said accurate interaction between said extracted first and second bio-entities and said extracted interaction word within said second level;
classifying said at least one triplet as true as a result of said second probability value meeting said threshold probability value, and
classifying said at least one triplet as false as a result of said second probability value failing to meet said threshold probability value.

12. A computer-implemented method as in claim 10, further comprising instructions for:
receiving a structured form format corresponding to said plurality of known bio-entity strings; and
storing said at least one extracted triplet in said structured form format as a result of a classification of said at least one extracted triplet being true, said storing facilitating retrieval of said at least one extracted, true triplet.

13. A computer-implemented method as in claim 10, further comprising:
said simplified pattern of said second level automatically created by replacing said non-triplet word strings with a wildcard that permits extraction of non-annotated data not containing said non-triplet word strings.

14. A computer-implemented method as in claim 10, further comprising instructions for:
establishing a third level in said hierarchical structure, said third level having a third decision node,
said third level being a further simplified pattern of said second level to capture triplets that are not identical to said at least one extracted triplet,
said third decision node having a different level of detail than said first and second decision nodes; and
as a result of said extracted textual clause failing to match said second level, extracting said at least one triplet from said extracted textual clause by attempting to match said extracted textual clause to said third level;
identifying extraction of said at least one triplet as true if said extracted textual clause matches said third level; and
identifying extraction of said at least one et as false if said extracted textual clause fails to match said third level.

15. A computer-implemented method as in claim 14, further comprising:
said further simplified pattern of said third level automatically created by grouping analogous interaction words with said interaction word to permit extraction of non-annotated data not containing said interaction word but containing one of said analogous interaction words.

16. A computer-implemented method as in claim 10, further comprising:
said first bio-entity being a first protein,
said second bio-entity being a second protein, and
said interaction word associating said first protein to said second protein.

17. A computer-implemented method as in claim 10, further comprising:
said decision support tool being a decision tree.

18. A computer-implemented method as in claim 10, further comprising:
the step of automatically building said decision support tool further based on relationships among additional dependencies among said true and false patterns in said annotated data.

19. One or more non-transitory, tangible computer-readable media having computer-executable instructions for performing a method by running a software program on a computer, the computer operating under an operating system, the method including issuing instructions from the software program to extract textual relationships or semantic information from non-annotated data by natural language processing and graph theoretic algorithm, the instructions comprising:
receiving a plurality of known textual strings and a plurality of interaction word strings;
receiving annotated text as training data that contains true and false patterns;
automatically building a decision support tool based on said true and false patterns to which said non-annotated data can he parsed, said decision support tool including at least a first level and a second level, said first level having a first decision node, said second level having a second decision node, said first and second decision nodes each associated with at least a portion of said true and false patterns;

receiving said non-annotated data;

extracting a textual clause of said non-annotated data that contains non-triplet word strings and at least one triplet, said at least one triplet including a first textual string, a second textual string, and an interaction word, wherein said interaction word indicates a possible relationship between said first textual string and said second textual string;

automatically parsing said extracted textual clause through said decision support tool to obtain a plurality of components based on dependencies among said plurality of components, extracting said at least one triplet from said plurality of components by attempting to match said plurality of components of said parsed, extracted textual clause to said first level of said decision support tool;

identifying extraction of said at least one triplet as true if said extracted textual clause matches said first level of said decision support tool;

identifying extraction of said at least one triplet as false if said extracted textual clause fails to match said first level of said decision support tool;

as a result of said plurality of components failing to match said first level of said decision support tool, extracting said at least one triplet from said plurality of components by attempting to match said plurality of components to said second level of said decision support tool;

identifying extraction of said at least one triplet as true if said plurality of components matches said second level of said decision support tool, said second level of said decision support tool being a simplified pattern of said first level of said decision support tool to capture textual clauses that are not identical to said extracted textual clause; and identifying extraction of said at least one triplet as false if said plurality of components fails to match said second level of said decision support tool.

20. A computer-implemented software application as in claim 19, further comprising instructions for:

establishing a threshold probability value based on probable accuracy retrieved from said decision support tool;

said step of extracting said at least one triplet from said extracted textual clause by attempting to match said extracted textual clause to said first level, including:

tagging said extracted textual clause with a first probability value based on said accurate interaction between said extracted first and second bio-entities and said extracted interaction word within said first level;

classifying said at least one triplet as true as a result of said first probability value meeting said threshold probability value, and classifying said at least one triplet as false as a result of said first probability value failing to meet said threshold probability value;

said step of extracting said at least one triplet from said extracted textual clause by attempting to match said extracted textual clause to said second level, including:

tagging said extracted textual clause with a second probability value based on said accurate interaction between said extracted first and second bio-entities and said extracted interaction word within said second level;

classifying said at least one triplet as true as a result of said second probability value meeting said threshold probability value, and classifying said at least one triplet as false as a result of said second probability value failing to meet said threshold probability value.

* * * * *

UNITED STATES PATENT AND TRADEMARK OFFICE
CERTIFICATE OF CORRECTION

PATENT NO. : 8,886,522 B2  
APPLICATION NO. : 13/971145  
DATED : November 11, 2014  
INVENTOR(S) : Jinfeng Zhang Page 1 of 1

It is certified that error appears in the above-identified patent and that said Letters Patent is hereby corrected as shown below:

In the Claims

Column 18, Claim 10, Line 49 should read as follows:

tic bio-entity relationships or patterns from non-annotated

Column 20, Claim 14, Line 29 should read as follows:

identifying extraction of said at least one triplet as false if said

Signed and Sealed this  
Twenty-fourth Day of March, 2015

Michelle K. Lee  
*Director of the United States Patent and Trademark Office*